(12) United States Patent
Izawa et al.

(10) Patent No.: US 9,182,366 B2
(45) Date of Patent: Nov. 10, 2015

(54) GAS DETECTION APPARATUS AND GAS DETECTION METHOD

(75) Inventors: Kuniyuki Izawa, Mino (JP); Kenichi Yoshioka, Mino (JP); Chizumi Kitagawa, Mino (JP)

(73) Assignee: Figaro Engineering Inc., Osaka (JP)

( * ) Notice: Subject to any disclaimer, the term of this patent is extended or adjusted under 35 U.S.C. 154(b) by 684 days.

(21) Appl. No.: 13/478,136

(22) Filed: May 23, 2012

(65) Prior Publication Data

US 2012/0297860 A1 Nov. 29, 2012

(30) Foreign Application Priority Data

May 26, 2011 (JP) ................................ 2011-117795

(51) Int. Cl.
*G01N 27/12* (2006.01)
*G01N 33/00* (2006.01)

(52) U.S. Cl.
CPC .......... *G01N 27/124* (2013.01); *G01N 33/0013* (2013.01); *G01N 27/128* (2013.01)

(58) Field of Classification Search
CPC . G01N 27/128; G01N 27/12; G01N 27/4074; G01N 33/0027; G01N 33/004
See application file for complete search history.

(56) References Cited

U.S. PATENT DOCUMENTS

| | | | | | |
|---|---|---|---|---|---|
| 4,775,838 | A | * | 10/1988 | Mizuta et al. | 324/468 |
| 5,551,283 | A | * | 9/1996 | Manaka et al. | 73/31.01 |
| 5,759,367 | A | * | 6/1998 | Matsuura et al. | 204/424 |
| 6,111,280 | A | * | 8/2000 | Gardner et al. | 257/253 |
| 6,128,945 | A | * | 10/2000 | Shioiri et al. | 73/31.06 |
| 2004/0026408 | A1 | * | 2/2004 | Morinaga et al. | 219/497 |
| 2009/0151429 | A1 | * | 6/2009 | Jun et al. | 73/31.06 |
| 2011/0257898 | A1 | * | 10/2011 | Ooishi | 702/23 |
| 2012/0287962 | A1 | * | 11/2012 | Ooishi | 374/37 |

FOREIGN PATENT DOCUMENTS

| | | |
|---|---|---|
| JP | 1-221649 A | 9/1989 |
| JP | 3087982 B2 | 9/2000 |
| JP | 2001-330577 A | 11/2001 |
| JP | 2003-232760 A | 8/2003 |
| JP | 4401445 B2 | 1/2010 |

* cited by examiner

*Primary Examiner* — Harshad R. Patel
*Assistant Examiner* — Punam Roy
(74) *Attorney, Agent, or Firm* — Keating & Bennett, LLP

(57) ABSTRACT

A gas is detected using a MEMS gas sensor. The electrical power to a heater in the gas sensor is changed between a low level, a high level suitable for detection of detection target gas, and a 0 level, and, therefore, poisonous gas is evaporated or oxidized at the low level, and the detection target gas is detected at the high level.

9 Claims, 4 Drawing Sheets

GAS DETECTION APPARATUS AND GAS DETECTION METHOD

BACKGROUND OF THE INVENTION

1. Field of the Invention

The present invention relates to detection of a gas using a MEMS gas sensor, and particularly relates to prevention of poisoning by organic solvent, silicone vapor, or the like.

2. Description of Related Art

It is known that silicone vapor poisons a gas sensor. Known countermeasures against this problem include a technique for removing poisonous gas using a filter made of activated carbon or the like (Patent Document 1: JP 3087982) and a technique for causing poisonous gas to decompose on a surface portion of a gas sensor (Patent Document 2: JP 4401445). Furthermore, the present inventor found that, in the case of a MEMS gas sensor, organic solvent such as ethanol also acts as poisonous gas.

Although a filter is effective for the prevention of poisoning, when the filter is exposed to a high concentration of poisonous gas for a long period of time, the poisonous gas passes through the filter and reaches inside the gas sensor.

CITATION LIST

Patent Documents

[Patent Document 1] JP 3087982
[Patent Document 2] JP 4401445

SUMMARY OF THE INVENTION

It is an object of the present invention to prevent poisoning of a MEMS gas sensor by organic solvent, silicone vapor, or the like.

The present invention is directed to a gas detection apparatus, including: a MEMS gas sensor provided with a gas detection portion having a heater on an insulating film on a surface of a silicon substrate, and a cavity directly below the insulating film around the gas detection portion; a power source; and a drive circuit for the MEMS gas sensor; the drive circuit changing an electrical power to the heater between a low level suitable for evaporation or oxidization of poisonous gas, a high level suitable for detection of detection target gas, and a 0 level.

Also, the present invention is directed to a method for detecting a gas using a gas detection apparatus including a MEMS gas sensor provided with a gas detection portion having a heater on an insulating film on a surface of a silicon substrate, and a cavity directly below the insulating film around the gas detection portion, a power source, and a drive circuit for the MEMS gas sensor, the method including the step of: causing the drive circuit to change an electrical power to the heater between a low level, a high level suitable for detection of detection target gas, and a 0 level, and thereby evaporating or oxidizing poisonous gas at the low level and detecting the detection target gas at the high level.

According to the present invention, the gas detection portion is heated at the low level, and, therefore, the poisonous gas attached to the gas detection portion is evaporated or oxidized, and poisoning of the gas detection portion is prevented. In the case where the poisonous gas is silicone vapor, if the silicone vapor decomposes, silica accumulates on the gas detection portion. Thus, the silicone vapor is evaporated from the gas detection portion. An organic solvent such as ethanol also causes poisoning of the MEMS gas sensor. Note that the power consumption of the MEMS sensor increases when the gas detection portion is kept at a high temperature for a long period of time. Accordingly, the poisoning is prevented by evaporating or oxidizing the organic solvent at the low level. It is assumed that, in this specification, ranges indicated by "to" define a range including the lower limit or more and the upper limit or less. The description regarding the gas detection apparatus in this specification is directly applicable to the gas detection method, and, conversely, the description regarding the gas detection method is directly applicable to the gas detection apparatus.

It is preferable that the drive circuit changes the electrical power to the heater in order from the low level, to the high level, and then to the 0 level. The poisonous gas accumulated at the 0 level is evaporated or oxidized at the low level, and the detection target gas, which is different from the poisonous gas, is detected at the high level.

Furthermore, it is preferable that the drive circuit does not perform detection of the detection target gas at the low level. Contrary to conventional examples in which methane is detected at the high level and CO is detected at the low level, the low level is applied in order to treat the poisonous gas, and a gas is detected at the low level only when detecting organic solvent as the poisonous gas and determining whether or not to perform heating at the low level, for example.

A temperature of the gas detection portion at the low level is preferably 60 to 200° C., and particularly preferably 60 to 120° C. For example, since the boiling point of silicone vapor is approximately 200° C., and the boiling point of organic solvent such as ethanol is 100° C. or lower, the poisonous gas is evaporated or oxidized at these temperatures.

It is preferable that the detection portion has a $SnO_2$ film supporting a noble metal catalyst, an electrode in contact with the $SnO_2$ film, and an oxidation catalyst film covering the $SnO_2$ film. The oxidation catalyst film oxidizes and removes poisonous gas such as organic solvent at the low level. Accordingly, also in the case where $SnO_2$, which is a mild oxidation catalyst, is used, removal of the poisonous gas is facilitated.

It is preferable that, when restarting the gas detection apparatus from a stopped state, the drive circuit supplies the electrical power at the low level to the heater for a period of time longer than a supply time after completion of the restart. Accordingly, the poisonous gas accumulated in the stopped state is removed.

It is preferable that the drive circuit determines presence or absence of the poisonous gas based on a resistance of the $SnO_2$ film with the electrical power to the heater at the low level or at a level between the low level and the high level, and, in a case where it is determined that the poisonous gas of at least at a predetermined concentration is present, changes the electrical power to the heater between the low level, the high level, and the 0 level in a cyclic manner, and, in a case where it is determined that the poisonous gas of at least at a predetermined concentration is not present, changes the electrical power to the heater between the high level and the 0 level in an alternate manner. Accordingly, the power consumption is reduced by omitting the heating at the low level when the concentration of the poisonous gas is low. When performing the heating at the low level, the heating of the heater is preferably changed in order from the low level, to the high level, and then to the 0 level in a cyclic manner, but heating may be performed by alternating between a period during which the 0 level and the low level are mixed and the high level.

BRIEF DESCRIPTION OF THE DRAWINGS

FIG. 6A shows electrical power for heating, and FIG. 6B shows a temperature of a gas detection portion.

DETAILED DESCRIPTION OF THE INVENTION

Figure 1:
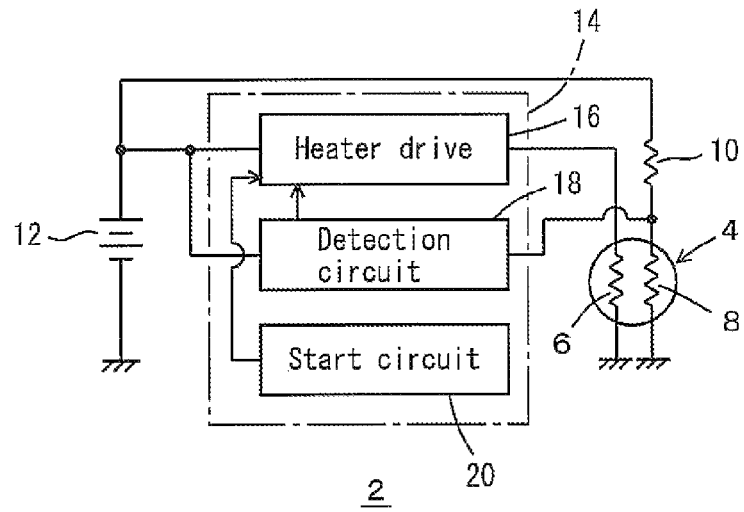
FIG. 1 is a block diagram of a gas detection apparatus using a $SnO_2$ MEMS gas sensor.

Hereinafter, an optimal embodiment for carrying out the present invention will be described, but the invention is not limited thereto, and modifications are possible by adding matters known to those skilled in the art to the description of the specification and the drawings.

Embodiment

FIGS. 1 to 7 show a gas detection apparatus 2 and its modified examples according to the embodiment. In the drawings, 4 denotes a SnO₂ MEMS gas sensor (hereinafter, a gas sensor 4) that is provided with a heater 6 and a SnO₂ film 8. 10 denotes a load resistor, 12 denotes a battery that functions as a power source, and 14 denotes a microcomputer as a drive circuit for the gas sensor 4, the microcomputer functioning as a heater drive 16, a detection circuit 18, and a start circuit 20. The heater drive 16 controls the electrical power to the heater 6 through PWM (pulse width modulation) or the like, and, for example, drives the heater 6 in 30-second cycles in order from a low level (0.4 seconds), to a high level (0.1 seconds), and then to a 0 level. The detection circuit 18 detects methane as detection target gas based on the resistance of the SnO₂ film 8 or an amount corresponding thereto, which in this embodiment is the voltage applied to the SnO₂ film 8, when the heater electrical power is at the high level. The resistance of the SnO₂ film 8 or an amount corresponding thereto is hereinafter referred to as a sensor output. The detection circuit 18 is provided with an AD converter, and determines the concentration of methane, for example, by determining the resistance of the SnO₂ film and comparing this value with various reference values. Alternatively, the detection circuit 18 may determine the concentration of the poisonous gas based on the sensor output at the low level. The start circuit 20 transmits a signal to the heater drive 16 so as to heat the sensor 4 at the low level for 1 to 20 seconds (4 seconds in this embodiment), which is longer than the 0.4 seconds applied in usual cases, when starting the gas detection apparatus 2 that has been stopped, such as when the battery 12 and the microcomputer 14 are connected via a switch (not shown) or the like, for example.

Figure 2:
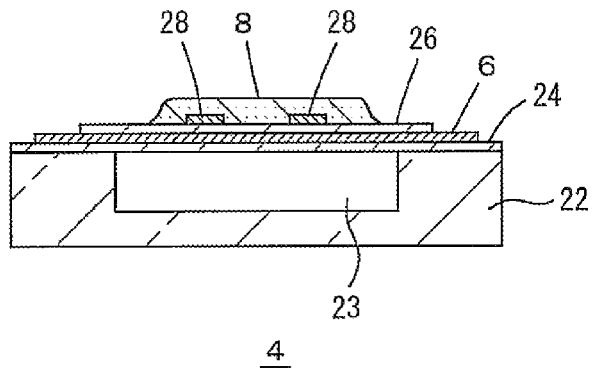
FIG. 2 is a cross-sectional view showing a main portion of the SnO₂ MEMS gas sensor.

FIG. 2 shows the structure of the SnO₂ MEMS gas sensor 4, in which one face of a silicon substrate 22 has an insulating film 24 made of silica, tantalum oxide, or the like, and a cavity 23 is formed directly below the insulating film 24. The heater 6 in the form of a film such as a Pt film is disposed on the insulating film 24 above the cavity 23, and is covered with a second insulating film 26. A pair of electrodes 28 made of Pt films or the like and the SnO₂ film 8 are arranged on the insulating film 26. The sensor 4 may have any structure and may be made of any material, and may include other metal oxide semiconductors made of WO₃, In₂O₃, or the like instead of SnO₂. In this embodiment, the SnO₂ film 8 has a film thickness of 30 μm, and contains 1.5 mass % of Pd with respect to 100 mass % of SnO₂. Furthermore, a housing (not shown) of the gas sensor 4 may be provided with a filter made of, for example, activated carbon, silica gel, zeolite, and, in particular, high-silica zeolite for ethanol adsorption.

Figure 3:
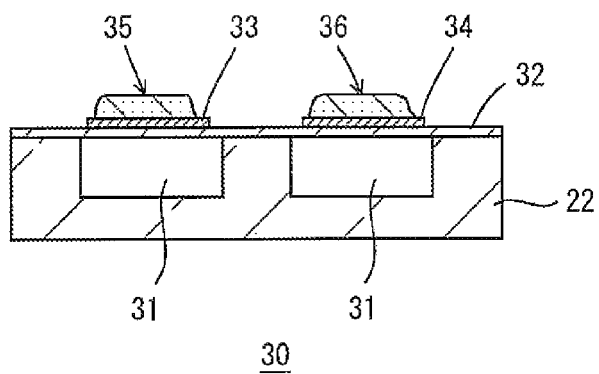
FIG. 3 is a cross-sectional view showing a main portion of a contact combustion-type MEMS gas sensor.
Figure 4:
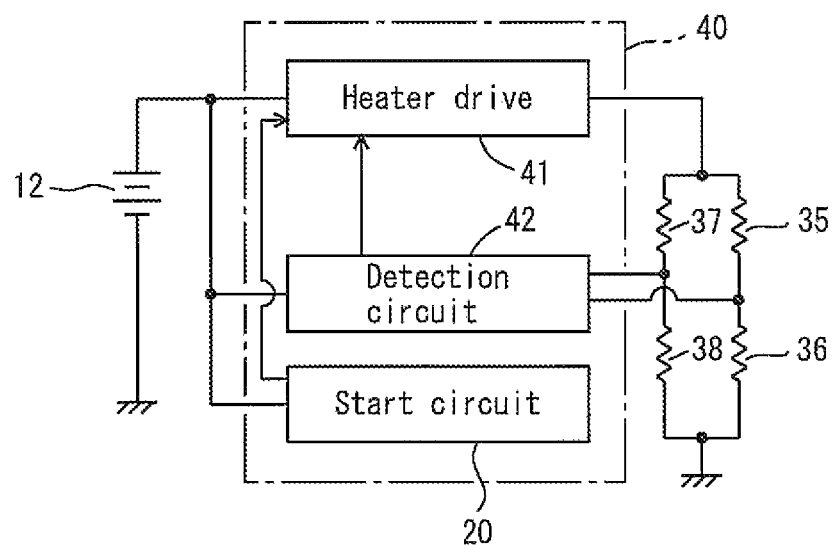
FIG. 4 is a block diagram of a gas detection apparatus using a contact combustion-type MEMS gas sensor.

FIG. 3 shows a contact combustion-type MEMS gas sensor 30, and FIG. 4 shows its drive circuit, where the same reference numerals as those in FIGS. 1 and 2 denote the same constituent components. One face of the silicon substrate 22 has an insulating film 32 made of silica, tantalum oxide, or the like, and a pair of or one cavity 31 is formed directly below the insulating film 32. A pair of heaters 33 and 34 in the form of Pt films or the like are arranged on the insulating film 32 above the cavity 31. The heater 33 is covered with a thick film made of a material in which a carrier such as boehmite or γ alumina supports an oxidation catalyst such as Pt or Pd, forming a detection piece 35. The heater 34 is covered with a thick film in which a carrier such as boehmite or γ alumina is contained, forming a reference piece 36. The contact combustion-type MEMS gas sensor 30 may have any structure and may be made of any material.

In the drive circuit in FIGS. 4, 37 and 38 denote resistors, and 40 denotes a microcomputer. A heater drive 41 drives a bridge circuit of the detection piece 35 and the reference piece 36 and the resistors 37 and 38 through PWM or the like, and, for example, drives the detection piece 35 and the reference piece 36 in 30-second cycles in order from a low level, to a high level, and then to a 0 level. In synchronization with a voltage applied at the high level to the detection piece 35 and the reference piece 36, a detection circuit 42 performs AD conversion on the output of the bridge circuit, and determines the concentration of methane, hydrogen, isobutane, mercaptan, or the like. If the sensor 30 is provided with a filter, the detection circuit 42 may determine whether or not the concentration of the poisonous gas is a predetermined value or more based on the output of the bridge circuit at the low level.

Figure 5:
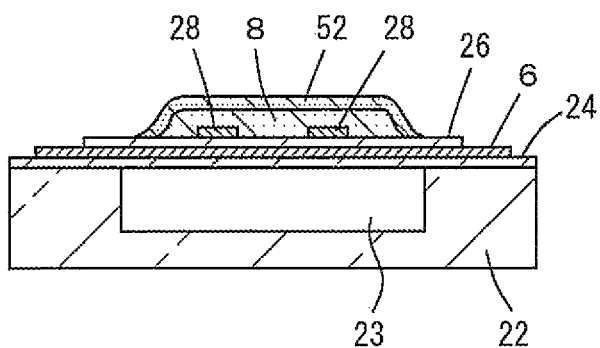
FIG. 5 is a cross-sectional view showing a main portion of a SnO₂ MEMS gas sensor covered with an oxidation catalyst film.

A SnO₂ MEMS gas sensor 50 in FIG. 5 is formed by covering the SnO₂ film 8 in the gas sensor in FIG. 2 with an oxidation catalyst film 52. The oxidation catalyst film 52 may be a noble metal catalyst such as Pt or Pd supported on a carrier such as alumina, a transition metal oxide such as MnO₂, Mn₂O₃, MnO, LaCoO₃, or LaNiO₃ having a higher oxidation activity than SnO₂, or a noble metal catalyst such as Pt or Pd supported on a transition metal oxide.

Figure 6A:
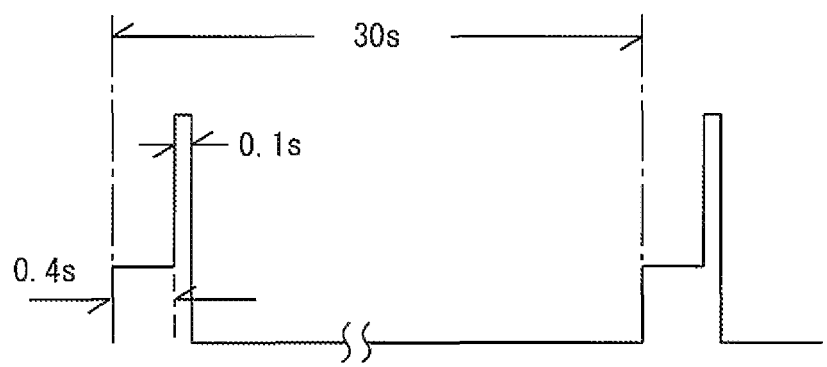
FIGS. 6A and 6B show waveform charts illustrating a heating pattern of an MEMS gas sensor according to an embodiment, where
Figure 6B:
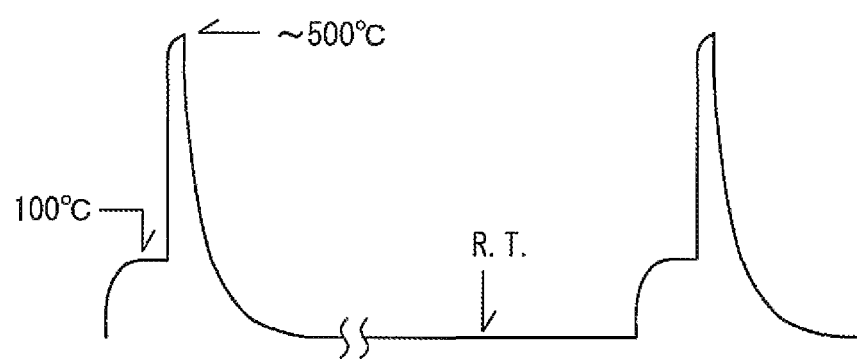
Figure 7:
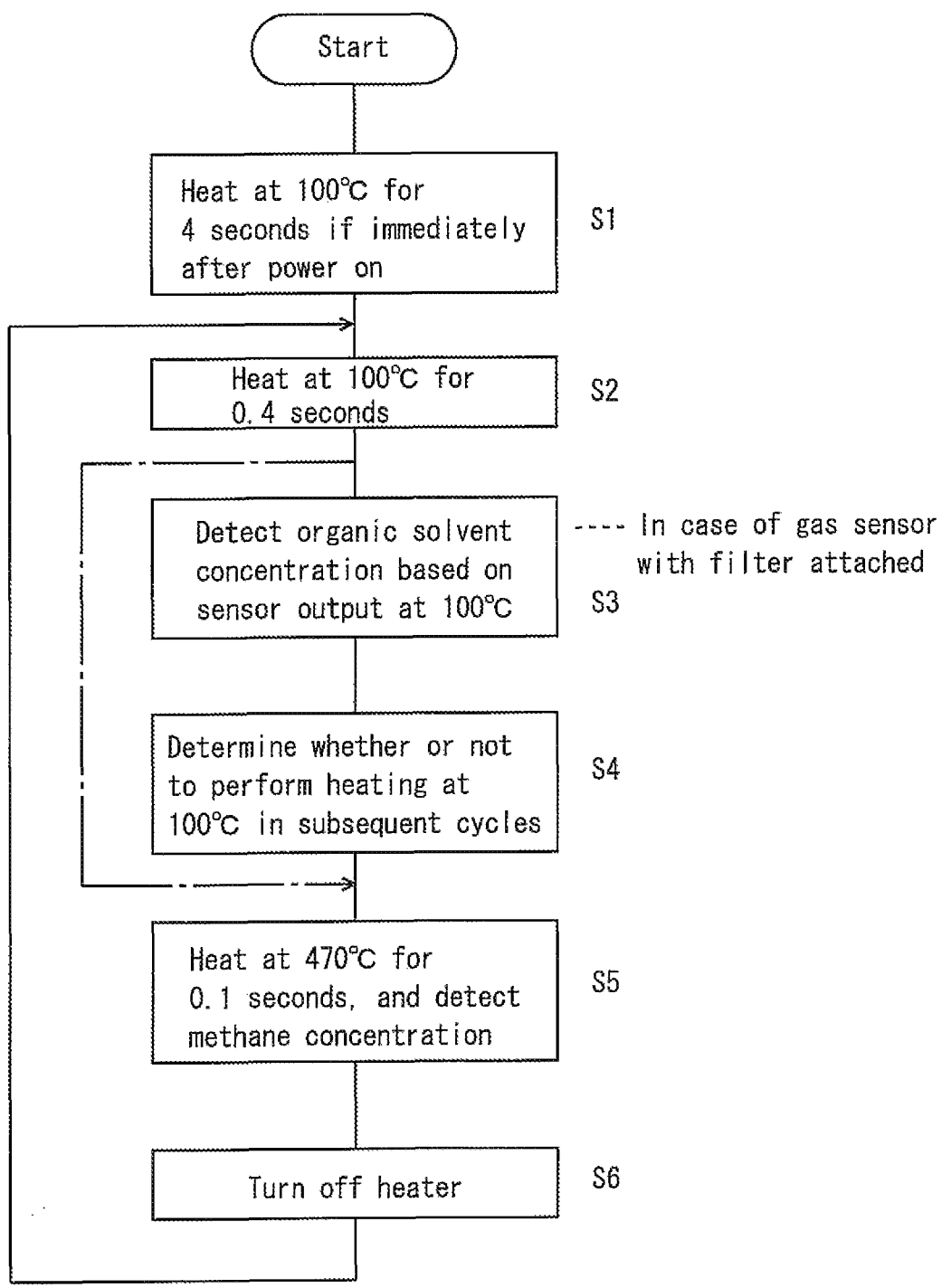
FIG. 7 shows a flowchart illustrating an algorithm of the embodiment.

FIGS. 6A, 6B, and 7 show drive algorithms of the gas sensors 4, 30, and 50. In this example, the temperature of the SnO₂ film 8 or the detection piece 35 at the low level is set to 100° C., the temperature of the SnO₂ film 8 or the detection piece 35 at the high level is set to, for example, 470° C., and the temperature at the high level is set to generally 300° C. to 550° C. Furthermore, an operation that heats the sensor at a predetermined level or to a predetermined temperature refers to an operation that heats the SnO₂ film 8 or the detection piece 35 with a predetermined electrical power or to a predetermined temperature. When the power is turned on, the sensor is heated at the low level, for example, for 4 seconds, and preferably for 1 to 20 seconds, and, therefore, poisonous gas that has accumulated on the SnO₂ film 8 or the detection piece 35 while being allowed to stand is evaporated or oxidized (Step 1). Next, the gas sensor 4, 30, or 50 is driven, for example, in 30-second cycles such that the heater operates at the low level for first 0.4 seconds, and preferably 0.1 to 2 seconds (Step 2), operates at the high level for next 0.1 seconds, and preferably 0.02 to 0.5 seconds (Step 5), and then is turned off for the remaining time (Step 6). The 30-second cycle is adopted in order to set the methane detection delay to, for example, approximately 30 seconds, and the cycle is assumed to be, for example, 5 seconds to 10 minutes. The heating time at the low level is set more broadly to 0.1 to 4 seconds, even more broadly to 0.1 to 10 seconds.

During heating at the low level, the sensor is heated, for example, at 100° C. If the poisonous gas is silicone vapor, its boiling point is in many cases slightly lower than 200° C., and at 100° C. the silicone vapor is evaporated from the sensor without decomposition. Thus, the poisoning is prevented. If the poisonous gas is organic solvent such as ethanol, its boiling point is in many cases slightly lower than 100° C., and at 100° C. the organic solvent is evaporated from the sensor. A noble metal catalyst and a transition metal oxide catalyst such as $MnO_2$ have an ability to oxidize organic solvent such as ethanol even at a temperature lower than 100° C., and oxidize and remove the organic solvent adhering to the sensor at the low level. Poisoning by an organic solvent is presumed to proceed by the following mechanism in the case of ethanol. That is to say, ethanol is transformed into an easily polymerizable compound such as acetaldehyde, this compound is polymerized, and a poisonous material that is difficult to remove accumulates.

In an environment where poisoning by organic solvent is a problem, the sensor is preferably provided with a filter made of activated carbon or the like. The sensor is sensitive to the organic solvent at the low level, and, therefore, the concentration of the poisonous gas is determined at the low level or at a level between the low level and the high level, where, if the concentration is a predetermined value or more, the heating at the low level is performed in the subsequent cycles, and, if the concentration is less than the predetermined value, the heating at the low level may be omitted in the subsequent cycles (Steps 2 and 3). This determination is performed every 100 cycles, for example, and preferably every 10 to 1000 cycles. Steps 2 and 3 are provided in order to reduce power consumption, but are problematic in that poisonous gas may accumulate on the sensor, and, therefore, Steps 2 and 3 may be omitted.

Table 1 shows the influence of silicone poisoning under the above-described drive conditions. Air containing silicone vapor (8 ppm of siloxane D4) was set as a poisoning atmosphere, sensors were driven in the poisoning atmosphere for 10 days, and the change in performance before and after the silicone poisoning was determined Note that the number of sensors used in each case was 20, and the results are shown as an average of these sensors. Table 2 shows results obtained when the heating temperature at the low level for the sensors in FIG. 2 was changed. According to the table, the influence of the poisoning was significant if the heating at the low level was not performed, a best result was obtained if the low level was set to 80° C. or 100° C., a slightly worse result was obtained at 120° C., and a result similar to that in the case where the heating at the low level was not performed was obtained at 300° C. In the case of the $SnO_2$ sensors in FIG. 2, if the sensors were allowed to stand in a poisoning atmosphere, and then taken out of the poisoning atmosphere and heated at 100° C. for 4 seconds, the output ratio before and after silicone poisoning was 0.9 with respect to 3000 ppm of methane, and was 0.75 with respect to 1000 ppm of hydrogen. Furthermore, if the heating at 100° C. for 4 seconds was not performed, the output ratio before and after silicone poisoning was 0.6 with respect to 3000 ppm of methane, and was 0.3 with respect to 1000 ppm of hydrogen.

TABLE 1

| | Output ratio before and after silicone poisoning | |
|---|---|---|
| Sensor type | Methane 3000 ppm | Hydrogen 1000 ppm |
| $SnO_2$ (FIG. 2) | 0.95 | 0.85 |
| Contact combustion-type (FIG. 3) | 0.85 | 0.95 |
| $SnO_2$ + oxidation catalyst (FIG. 5) | 0.95 | 0.90 |

Sensors: without filter
Drive conditions: 100° C. for 0.4 seconds, 470° C. for 0.1 seconds, and room temperature for remaining time, in 30-second cycles
Poisoning conditions: exposed to 8 ppm of silicone vapor (D4) for 10 days
Output: ratio between resistances after and before poisoning in specified atmosphere for $SnO_2$ sensors; ratio between bridge circuit outputs after and before poisoning in specified atmosphere for contact combustion-type sensors
Oxidation catalyst film in FIG. 5 is 10 μm-thick $MnO_2$ film supporting 1 mass % of Pt.

TABLE 2

| | Output ratio before and after silicone poisoning | |
|---|---|---|
| Temperature at low level | Methane 3000 ppm | Hydrogen 1000 ppm |
| No low-level heating | 0.65 | 0.35 |
| 60° C. | 0.90 | 0.75 |
| 80° C. | 1.0 | 0.80 |
| 100° C. | 0.95 | 0.85 |
| 120° C. | 0.85 | 0.70 |
| 200° C. | 0.75 | 0.50 |
| 300° C. | 0.60 | 0.35 |

Sensors: $SnO_2$ sensor in FIG. 2 without filter
Poisoning conditions: exposed to 8 ppm of silicone vapor (D4) for 10 days
Drive conditions: low level for 0.4 seconds, 470° C. for 0.1 seconds, and room temperature for remaining time, in 30-second cycles
Output: ratio between resistances after and before poisoning in specified atmosphere A filter containing 150mg of granular activated carbon was attached to the $SnO_2$ sensors in FIGS. 2 and 5, and the resistance to ethanol poisoning was evaluated. Table 3 shows results for the sensors 4 in FIG. 2, and Table 4 shows results for the sensors 50 in FIG. 5. According to the tables, a best result was obtained if the low-level heating at 80° C. or 100° C. was performed, a slightly worse result was obtained at 120° C., and a considerably worse result was obtained at 300° C. Furthermore, if the heating at the low level was performed, the resistance to poisoning by ethanol in the sensors in FIG. 5 was better than that in the sensors in FIG. 2. The resistance to poisoning by acetaldehyde, toluene, or the like instead of by ethanol was checked, and it was found that the influence of the poisoning was reduced if the low-level heating at 80° C. or 100° C. was performed, and that the influence of the poisoning was further reduced if sensors were covered with an oxidation catalyst.

TABLE 3

| | Output ratio before and after ethanol poisoning | |
|---|---|---|
| Temperature at low level | Methane 3000 ppm | Hydrogen 1000 ppm |
| No low-level heating | 2.05 | 1.35 |
| 60° C. | 0.85 | 0.80 |
| 80° C. | 0.90 | 0.85 |
| 100° C. | 0.95 | 0.90 |
| 120° C. | 0.85 | 0.80 |
| 200° C. | 1.10 | 1.20 |
| 300° C. | 1.25 | 1.30 |

Sensors: $SnO_2$ sensor in FIG. 2, with filter containing 150 mg of granular activated carbon
Poisoning conditions: exposed to 3000 ppm of ethanol for 1 hour/day for 5 days
Drive conditions: low level for 0.4 seconds, 470° C. for 0.1 seconds, and room temperature for remaining time, in 30-second cycles
Output: ratio between resistances after and before poisoning in specified atmosphere

TABLE 4

| | Output ratio before and after ethanol poisoning | |
|---|---|---|
| Temperature at low level | Methane 3000 ppm | Hydrogen 1000 ppm |
| No low-level heating | 2.05 | 1.35 |
| 80° C. | 1.00 | 0.95 |
| 100° C. | 1.00 | 0.95 |
| 120° C. | 0.90 | 1.05 |
| 300° C. | 1.10 | 1.20 |

Sensors: $SnO_2$ sensor in FIG. 5 (covered with 10 μm-thick $MnO_2$ film supporting 1 mass % of Pt), with filter containing 150 mg of granular activated carbon
Poisoning conditions: exposed to 3000 ppm of ethanol for 1 hour/day for 5 days
Drive conditions: low level for 0.4 seconds, 470° C. for 0.1 seconds, and room temperature for remaining time, in 30-second cycles
Output: ratio between resistances after and before poisoning in specified atmosphere

TABLE 5

| | Output ratio before and after ethanol poisoning | |
|---|---|---|
| Temperature and time at low level | Methane 3000 ppm | Hydrogen 1000 ppm |
| 80° C. × 0.1 sec | 0.85 | 0.80 |
| 80° C. × 0.4 sec | 0.90 | 0.85 |
| 80° C. × 1.0 sec | 0.95 | 0.95 |
| 100° C. × 0.1 sec | 0.85 | 0.90 |
| 100° C. × 0.4 sec | 0.95 | 0.90 |
| 100° C. × 1.0 sec | 1.00 | 0.95 |

Sensors: $SnO_2$ sensor in FIG. 2, with filter containing 150 mg of granular activated carbon
Poisoning conditions: exposed to 3000 ppm of ethanol for 1 hour/day for 5 days
Drive conditions: low level for 0.4 seconds, 470° C. for 0.1 seconds, and room temperature for remaining time, in 30-second cycles
Output: ratio between resistances after and before poisoning in specified atmosphere Table 5 shows the influence of the heating time at the low level. A good effect was obtained with a heating time at the low level of 0.1 seconds, 0.4 seconds, or 1 second, and, therefore, it is seen that the heating time is preferably 0.1 to 2 seconds. Furthermore, the effect was slightly lower with a heating time of 0.1 seconds, and the power consumption increased with a heating time of longer than 1 second, and, therefore, it is seen that the heating time is more preferably 0.2 to 1 second. The heating time at the low level is set more broadly to 0.1 to 4 seconds, even more broadly to 0.1 to 10 seconds. It is seen from Tables 1 to 5 that the temperature at the low level is preferably 60 to 200° C., particularly preferably 60 to 120° C., more preferably 70 to 110° C., and most preferably 80 to 100° C. Note that the detection target gas may be of any type as long as it is different from the poisonous gas. Meanwhile, the temperature and the time at the high level may be determined as appropriate according to the detection target gas as long as the temperature is higher than that at the low level because poisoning does not occur at a temperature lower than that at the low level. In addition to the samples in Tables 1 to 5, the present inventor prepared samples in which the amounts of noble metal catalyst added to the $SnO_2$ film 8 were changed such that 3 mass % of Pd was contained with respect to 100 mass % of $SnO_2$ and such that 1.5 mass % of Pt was contained with respect to 100 mass % of $SnO_2$, and evaluated their resistances to poisoning. At that time, the same results were obtained in which the optimal temperature for the low-level heating is 80 to 100° C. and the low-level heating for 0.4 seconds provides sufficient effects. That is to say, the same conditions are applicable to the low-level heating regardless of the type or amount of noble metal supported on the $SnO_2$ film.

Hereinafter, the 0 level will be described in more detail. For example, a portable checker for flammable gas leakage may have a configuration in which the power is usually kept off and the heater electrical power of the gas sensor is kept at the 0 level in order to prevent poisoning by ethanol or the like, and, when the power is turned on, for example, the temperature is set to the low level at 100° C., for example, for 10 seconds, typically for 3 to 30 seconds, the temperature is then further increased to the high level at approximately 470° C. in approximately 30 milli seconds, which corresponds to the thermal time constant of the MEMS gas sensor, and a flammable gas is detected.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

DESCRIPTION OF REFERENCE NUMERALS

2 Gas detection apparatus
4, 50 $SnO_2$ MEMS gas sensor
6 Heater
8 $SnO_2$ film
10 Load resistor
12 Battery
14, 40 Microcomputer
16, 41 Heater drive
18, 42 Detection circuit
20 Start circuit
22 Silicon substrate
23, 31 Cavity
24, 26 Insulating film
28 Electrode
30 Contact combustion-type MEMS gas sensor
32 Insulating film
33, 34 Heater
35 Detection piece
36 Reference piece
37, 38 Resistor
52 Oxidation catalyst film

What is claimed is:
1. A gas detection apparatus, comprising:
a MEMS gas sensor provided with a gas detection portion having a heater on an insulating film on a surface of a silicon substrate, and a cavity directly below the insulating film around the gas detection portion;
a power source; and
a drive circuit for the MEMS gas sensor; wherein
the drive circuit is configured to change, during each of a plurality of cycles, the plurality of cycles having a duration of 5 seconds to 10 minutes, an electrical power to the heater between a low level suitable for evaporation or oxidization of poisonous gas operating for a period of time in a range of 0.1 second and 2 seconds, a high level suitable for detection of detection target gas operating for a period of time in a range of 0.02 second and 0.5 second, and a 0 level for a remaining time period of the respective cycle; and
the detection portion includes a $SnO_2$ film supporting a noble metal catalyst an electrode in contact with the $SnO_2$ film, and an oxidation catalyst film.
2. The gas detection apparatus according to claim 1, the drive circuit changing the electrical power to the heater in order from the low level, to the high level, and then to the 0 level.

3. The gas detection apparatus according to claim 1, the drive circuit not detecting the detection target gas at the low level.

4. The gas detection apparatus according to claim 1, a temperature of the gas detection portion at the low level being 60 to 200° C.

5. The gas detection apparatus according to claim 4, the temperature of the gas detection portion at the low level being 60 to 120° C.

6. The gas detection apparatus according to claim 1, wherein:
the oxidation catalyst film covers the $SnO_2$ film.

7. The gas detection apparatus according to claim 6, the drive circuit determining presence or absence of the poisonous gas based on a resistance of the $SnO_2$ film with the electrical power to the heater at the low level or at a level between the low level and the high level, and, in a case where it is determined that the poisonous gas of at least at a predetermined concentration is present, changing the electrical power to the heater between the low level, the high level, and the 0 level in a cyclic manner, and, in a case where it is determined that the poisonous gas of at least at a predetermined concentration is not present, changing the electrical power to the heater between the high level and the 0 level in an alternate manner.

8. The gas detection apparatus according to claim 1, when restarting the gas detection apparatus from a stopped state, the drive circuit supplying the electrical power at the low level to the heater for a period of time longer than a supply time after completion of the restart.

9. A method for detecting a gas using a gas detection apparatus including a MEMS gas sensor provided with a gas detection portion having a heater on an insulating film on a surface of a silicon substrate, and a cavity directly below the insulating film around the gas detection portion, a power source, and a drive circuit for the MEMS gas sensor,
the method comprising the step of: causing the drive circuit to change, during each of a plurality of cycles, the plurality of cycles having a duration of 5 seconds to 10 minutes, an electrical power to the heater between a low level operating for a period of time in a range of 0.1 second to 2 seconds, a high level suitable for detection of detection target gas operating for a period of time in a range of 0.02 second and 0.5 second, and a 0 level for a remaining time period of the respective cycle, and thereby evaporating or oxidizing poisonous gas at the low level and detecting the detection target gas at the high level; wherein
the detection portion includes a $SnO_2$ film supporting a noble metal catalyst an electrode in contact with the $SnO_2$ film, and an oxidation catalyst film.

* * * * *